US012761132B2

(12) United States Patent
Mazega Figueredo et al.

(10) Patent No.: US 12,761,132 B2
(45) Date of Patent: Oct. 13, 2026

(54) FORMULATION FOR COUNTING AND MORPHOLOGICAL-BASED INFERENCING OF ERYTHROCYTES AND PLATELETS AND METHOD OF MAKING AND USING SAME

(71) Applicant: Hi Technologies Ltda., Curitiba (BR)

(72) Inventors: Marcus Vinicius Mazega Figueredo, Curitiba (BR); Sergio Renato Rogal Júnior, Curitiba (BR); Aléxia Thamara Gasparin, Curitiba (BR); Claudiane Isabel Franco Araujo, Curitiba (BR); Erika Bergamo Santiago, Curitiba (BR); Luís Felipe Hartmann, Curitiba (BR); Adriano Artur Timm, Curitiba (BR); Ivan Lucas Reis Silva, Curitiba (BR); Flavia Zhu Teng, Curitiba (BR); João Victor Predebon, Curitiba (BR)

(73) Assignee: Hi Technologies Ltda., Curitiba (BR)

( * ) Notice: Subject to any disclaimer, the term of this patent is extended or adjusted under 35 U.S.C. 154(b) by 824 days.

(21) Appl. No.: 18/069,404

(22) Filed: Dec. 21, 2022

(65) Prior Publication Data

US 2023/0204487 A1 Jun. 29, 2023

(30) Foreign Application Priority Data

Dec. 23, 2021 (BR) .......................... 1020210262893

(51) Int. Cl.

| | |
|---|---|
| ***G01N 15/14*** | (2024.01) |
| ***G01N 33/49*** | (2006.01) |
| ***G01N 33/50*** | (2006.01) |
| *G01N 15/01* | (2024.01) |

(52) U.S. Cl.

CPC ............. *G01N 15/14* (2013.01); *G01N 33/49* (2013.01); *G01N 33/5094* (2013.01); *G01N 2015/012* (2024.01); *G01N 2015/018* (2024.01); *G01N 2015/1486* (2013.01); *Y10T 436/101666* (2015.01)

(58) Field of Classification Search

CPC ............. G01N 15/14; G01N 2015/018; G01N 2015/1486; G01N 33/5094; G01N 33/49; G01N 2015/012; Y10T 436/10; Y10T 436/101666; Y10T 436/106664; Y10T 436/108331; Y10T 436/2525; Y10T 436/25625

USPC ........... 436/8, 10, 16, 18, 63, 166, 176, 179; 252/408.1

See application file for complete search history.

(56) References Cited

U.S. PATENT DOCUMENTS 4,213,876 A 7/1980 Crews et al.
4,405,719 A * 9/1983 Crews ...................... A01N 1/10 436/17
4,528,274 A * 7/1985 Carter ................ G01N 33/5094 436/63
5,227,304 A * 7/1993 Wong ................. G01N 33/5094 436/179
6,114,173 A 9/2000 Zelmanovic et al.
6,524,858 B1 2/2003 Zelmanovic et al.
2004/0241769 A1* 12/2004 Crews ................ G01N 15/1456 435/270

FOREIGN PATENT DOCUMENTS

JP H0225150 B2 5/1990

OTHER PUBLICATIONS

BioGnost Ltd., Hayem's Solution Safety Data Sheet, Version 4, Date of Completion: Jun. 10, 2019; 16 pages.
Ricca Chemical Company LLC, "Rees and Ecker Blood Diluting Fluid Material Safety Data Sheet", Rev 1, Date Printed: Jan. 29, 2012; 4 pages.

* cited by examiner

*Primary Examiner* — Maureen Wallenhorst
(74) *Attorney, Agent, or Firm* — Calderon, Safran & Wright PC; Corinne Marie Pouliquen

(57) ABSTRACT

The invention relates to a formulation for counting and morphological-based inference of erythrocytes and platelets to for use in clinical analyses, in particular hemograms, with the purpose of counting both erythrocytes and platelets in a liquid medium, and performing qualitative inferences of erythrocyte and platelet morphology, through image processing in Point-of-Care devices or through an optical microscope. This formulation preserves the natural morphological characteristics of erythrocytes and platelets, and uses methylparaben, propylparaben, sodium chloride, sodium bicarbonate, bovine serum albumin (BSA), sodium citrate, potassium citrate, $K_2EDTA$ and deionized water, which is advantageous in terms of operational simplicity and low cost.

4 Claims, No Drawings

FORMULATION FOR COUNTING AND MORPHOLOGICAL-BASED INFERENCING OF ERYTHROCYTES AND PLATELETS AND METHOD OF MAKING AND USING SAME

CROSS-REFERENCE TO RELATED APPLICATIONS AND CLAIM TO PRIORITY

This application is related to Patent Application No. 10 2021 026289 3 filed Dec. 23, 2021, in Brazil, the disclosure of which is incorporated herein by reference and to which priority is claimed.

FIELD OF THE INVENTION

The invention relates to a formulation for counting and morphological-based inference of erythrocytes and platelets. This can be used in clinical analyses, in particular hemograms, with the purpose of counting both erythrocytes and platelets at the same time in a liquid medium, and performing qualitative inferences of erythrocyte and platelet morphology, through image processing in Point-of-Care devices or through an optical microscope. The formulation can preserve the natural morphological characteristics of erythrocytes and platelets, bringing the advantages of simplicity of operation and low cost.

BACKGROUND OF THE INVENTION

As is of current knowledge in clinical analytics, Hayem's solution and Rees-Ecker diluting fluid are commercially available diluent solutions, indicated to count, in liquid medium, erythrocytes and platelets. However, none of them preserve the natural morphological characteristics of these cells. Thus, in order for the morphology of red blood cells in a blood sample to be visualized, it must be fixed, dried, and stained on a microscope slide. The same occurs so that the visualization of macroplatelets or platelet aggregates is possible. Thus, performing the blood count manually requires several steps. There is also a commercial formulation known as "diluent for platelets," composed of ammonium oxalate (1%) but which promotes the lysis of erythrocytes and so only the platelet count can be obtained with this formulation.

Conventional methodologies for performing blood counts include automated hematology analyzers that require a high initial investment cost, calibration, and a highly specialized professional, in addition, altered results provided by hematology analyzers must be confirmed by optical microscopy from blood smears, stained and fixed. Giving the high demand for daily exams and the frequent maintenance required by this equipment, and this prevents the use for Point-of-Care purposes, or in places with low demand. Furthermore, the liquid solutions used by automated methodologies for performing blood counts are not suitable for manual analyses.

Searching in the Brazilian and international patent databases, the following disclosures were found:

U.S. Pat. No. 6,114,173 discloses a reagent composition for quick identification and characterization of cross-linked erythrocytes and platelets in whole blood and a reliable method for automated hematology analyzers. The reagent composition includes a zwitterionic surfactant, a fluorophore known as Oxazine 750® and a buffer solution to maintain a pH between 7.2 and 7.8 and an osmolality of 292. This composition also includes Proclin 300® in approximate amounts that vary from 0.015 to 0.035% by mass and also sodium chloride in the range from 0.540 to 0.732% by mass.

However, this diluent has the disadvantage of introducing compounds with high added value, so they make the product more expensive and, being made for automated electronic equipment, it does not satisfactorily meet the needs of manual counting, not allowing qualitative evaluation of erythrocytes and platelets under optical microscopes.

U.S. Pat. No. 6,524,858 deals with a method to identify, analyze and quantify the cellular components of a whole blood sample in an automated hematology analyzer through flow cytometry, using an organic dye in the reagent solution. The document reveals that the diluent composition for the method to work must have from 250 to 330 milliosmoles and contain at least one of the following compounds: up to 0.42% by mass of sodium bicarbonate, up to 0.9% by mass of sodium chloride or potassium chloride and up to 4.9% of dipotassium salt of ethylenediaminetetraacetic acid.

However, the focus of the aforementioned patent is for automated methods of blood analysis, its use in manual methodologies is not appropriate and may also present compounds with high added value.

U.S. Pat. No. 4,213,876 discloses an azide-free multipurpose blood thinner developed especially for use in counting and sizing blood cells and in determining the concentration of hemoglobin and its collective indices and platelet parameters in a single blood sample. A chelating agent with bacteriostatic and fungistatic functions, a stabilizing agent that prevents the development of microorganisms and a metallic sulfate to suppress turbidity are used. The formulation is osmotically balanced to maintain cell stability and is detergent-free to prevent bubble formation that can interfere with platelet counts via electronic instrumentation, and the invention includes modifications and adjustments to the diluent formulation that enable use in veterinary applications. The diluent formulation is composed of anhydrous sodium chloride in an approximate amount of 0.5% by mass, dihydrogen sodium phosphate, disodium phosphate, anhydrous sodium sulfate, 8-hydroxyquinoline citrate, anhydrous procaine hydrochloride and distilled water, adjusted to act as a buffer at pH between 7.2 and 7.6 and osmolality between 316 and 330 milliosmoles/kg.

However, this diluent has the disadvantage of introducing compounds of high added value that make the product more expensive and, being developed for automated electronic equipment, it does not satisfactorily meet the needs of manual counting.

The invention described in patent number JPH0225150B2 has the objective of obtaining a suspension for blood platelet counting with simple operation and little time consumption, in which a specific erythroclast liquid and a specific liquid for erythrocyte membrane degradation is added to the blood. the erythroclast liquid is composed of alcohol, ethylenediamine tetraacetate and distilled water, which is then added to the blood sample to be examined, with the function of breaking up the erythrocytes. A diluent liquid to dissolve the erythrocyte membrane is added, containing dodecyl sulfate and alkaline chloride of characteristic isotonic with the blood, reducing the number of fragments of the previously degraded erythrocyte membrane, forming a suspension of platelets, which are counted in a particle counter.

However, this diluent has the limitation of serving only for platelet count, not allowing the joint counting of erythrocytes and platelets, since it destroys the membranes of erythrocyte cells. Furthermore, it has the drawback of requiring two pre-analytical steps to enable platelet counts.

SUMMARY OF THE INVENTION

The invention was developed to overcome the disadvantages, inconveniences and limitations of the previous solutions, being a diluent formulation that allows, in a quick time and in a single step of process, to perform cell counts and qualitative inferences of erythrocyte and platelet morphology, being particularly useful for exams with Point-of-Care purposes, bringing advantages of operational simplicity and low cost per evaluated sample.

Current solutions for erythrocyte and platelet counting present the technical problem of not preserving simultaneously the natural morphological characteristics of erythrocytes and platelets, which is solved by the invention, whose diluent formulation is formed by salts that mimic blood electrolytes, providing a partially isotonic environment to blood cells, which preserves the natural morphological characteristics of erythrocytes and platelets for a period of up to 45 minutes.

In current procedures there is a technical problem of high complexity for the visualization of the morphology of the red blood cells of the sample of interest, the same occurs for the visualization of platelets, macroplatelets, platelet aggregates or erythrocyte rouleaux. Several steps are necessary, such as counting cells in a hemocytometer, preparing a blood smear and staining the slide where sample must be previously fixed and dry, in addition to requiring a specialized professional to perform these activities. This problem was solved by the invention with the formulation of a diluent that simplifies the sample preparation, needing only to dilute the blood in the formulation in an adequate amount.

Another technical problem with previous solutions is that they do not allow qualitative and quantitative joint assessment of erythrocytes and platelets at the same time. Problem solved by the invention, whose elaborate formulation does not lyse the erythrocytes and does not form platelet aggregates, allowing the joint qualitative and quantitative analysis of platelets and erythrocytes.

The research and development of this formulation began with the idea of producing a reagent for counting platelets and erythrocytes in a liquid medium. Research began with the association of the Rees-Ecker formulation with formulation 2 of the fast panoptic. As a result, erythrocytes were stained pink and platelets maintained a whitish hue, a result considered satisfactory. On the other hand, this formulation showed low stability and, in less than 24 hours on the shelf, it formed precipitates due to the interaction of the eosin dye, contained in the fast panoptic, with the bright cresyl blue dye contained in the Rees-Ecker formulation. Seeking stability improvement, a new formulation was produced using the Rees-Ecker formulation as a base, being composed of sodium citrate, formaldehyde and water, with pH 5, removing the bright cresyl blue dye from its formulation. However, unsatisfactory stability results continued to be observed in relation to the eosin dye. A new formulation was prepared, using the Hayem's solution as a base, associated with eosin dye for visualization of erythrocytes. However, once again, unsatisfactory results were observed in relation to the stability of the formulation and, therefore, it was decided to remove the dye from the formulation.

Still in relation to the research and development of the formulation, the main blood electrolytes and their respective concentrations were taken into account to establish the base compounds of this formulation. Starting from the premise of developing an isotonic formulation to mimic blood serum, the following components were used: sodium citrate, potassium chloride, bovine serum albumin (BSA), potassium citrate and sodium bicarbonate. As a result, it was possible to observe erythrocytes and platelets, but the erythrocytes presented crenate morphology due to the concentration of salts being above the ideal. From this, the amount of water was increased, making the formulation partially isotonic, and the desired results were achieved. The subsequent addition of dipotassium salt of ethylenediaminetetraacetic acid ($K_2$EDTA), an anticoagulant recommended for hematology by CLSI (Clinical and Laboratory Standards Institute) and by the ISCH (International Council for Standardization in Hematology), as it is the best anticoagulant to preserve cell morphology, was aimed to allow the use of the formulation for counting and morphological inference of erythrocytes and platelets with fresh blood, and not just blood previously diluted in anticoagulant. In addition, it was found that BSA can be replaced by casein with similar results, but the production process becomes longer and more expensive. During the product development research, the formulation was tested with the blood of rodents and pets (such as dogs, cats and horses), working perfectly for counting and morphological inference of erythrocytes and platelets, thus being able to also be applied in the field of veterinary analyses. In addition, the stability of the formulation was studied when stored for long periods, it was found that the formulation of the invention remains stable for a period of up to 4 months, provided it is protected from light.

DETAILED DESCRIPTION OF THE PREFERRED EMBODIMENT(S)

The preparation of the formulation for counting and morphological inference of erythrocytes and platelets (final composition) consists of three steps, described below:

1) Preparation of the preservative formulation, by weighing methylparaben and propylparaben, followed by dilution in deionized water. The homogenization of the formulation is carried out on a thermal magnetic plate heated to 100° C., or an equivalent procedure, until complete dilution of the aforementioned compounds. This preservative formulation can be replaced by the addition of a commercially available product such as Proain 300® [5-chloro-2-methyl-4-isothiazolin-3-one and 2-methyl-4-isothiazolin-3-one (3% by mass) dispersed in modified glycol (93-95% by mass) and alkyl carboxylate (2-3% by mass)], but resulting in lower effectiveness;
2) Preparation of the isotonic formulation, by weighing sodium bicarbonate, sodium chloride, bovine serum albumin (BSA), sodium citrate, potassium citrate and $K_2$EDTA, followed by dilution in deionized water; and
3) Preparation of the final composition, by mixing the preservative formulation with the isotonic formulation, followed by optional filtration through No. 1 filter paper for better analysis results, and subsequent pH measurement, which must be in the range between 7.5 and 9.5.

The main characteristics and technological functions of the components used in the final composition are described below:

a) Methylparaben, used with a high degree of purity (analytical grade), molar mass of 152.15 g/mol, CAS number 99-76-3, commercially known as Nipagin®, has a preservative action, being one of the responsible for keeping the formulation free from contamination by microorganisms as it is biocidal and biostatic. When added in insufficient amounts, the final composition is colonized by invading microorganisms, and when added in excess, it promotes cell death;

b) Propylparaben, used with a high degree of purity (analytical grade), molar mass of 180.20 g/mol, CAS number 94-13-3, commercially known as Nipazol®, also has a preservative action and keeps the final composition free of contamination by microorganisms as it is biocidal and biostatic. When added in insufficient amounts, the final composition is colonized by invading microorganisms, and when added in large amounts, it promotes cell death. Practical tests have shown that the joint use of methylparaben and propylparaben has a synergistic action, and when used alone, unsatisfactory results such as cell death or solution contamination are obtained;

c) Sodium bicarbonate, used with a high degree of purity (analytical grade), molar mass of 84.01 g/mol and CAS number 144-55-8, is a source of bicarbonate and sodium electrolytes, which are among the main blood electrolytes. If added in small amounts, the final composition is no longer partially isotonic and cell lysis occurs, and if added in excess, there will be changes in erythrocyte morphology and cell lysis;

d) Sodium chloride, used with a high degree of purity (analytical grade), molar mass of 58.44 g/mol and CAS number 7647-14-5, is a source of chloride and sodium electrolytes, which are among the main blood electrolytes. If less than the minimum is added, the final composition is no longer partially isotonic and promotes cell lysis, and if added in an amount greater than the maximum, there will be changes in erythrocyte morphology and cell lysis;

e) Bovine serum albumin (BSA), used with a high degree of purity (analytical grade), molar mass of 66.4 g/mol and CAS number 9048-46-8, is used as a protein source for the formulation. During research and tests, it was verified that its use is not mandatory for the correct functioning of the final composition, but when used, it improves the morphological characteristics of the erythrocytes and increases the stability of the formulation. When added in excess, it promotes changes in erythrocyte morphology and cell lysis;

f) Sodium citrate, used with a high degree of purity (analytical grade), molar mass of 294.10 g/mol and CAS number 68-04-2, is used as a source of sodium. During research and tests it was verified that its addition is not mandatory for the functioning of the final composition, but when added it improves the morphological characteristics of the erythrocytes. If added beyond the stipulated maximum, it causes changes in erythrocyte morphology and cell lysis;

g) Potassium citrate, used with a high degree of purity (analysis standard), molar mass of 306.39 g/mol and CAS number 6100-056, is used as a source of potassium. During research and testing, it was verified that its addition is not mandatory for the final composition to work. It has the function of improving the morphological characteristics of erythrocytes, but when added in excess, it causes changes in erythrocyte morphology and cell lysis;

h) $K_2EDTA$, used with a high degree of purity (analytical grade), molar mass of 404.45 g/mol and CAS number 25102-12-9 prevents clotting of the blood sample. When added in small amounts, the formation of platelet aggregates occurs, which causes errors in the platelet count, and when added in excess, it promotes changes in erythrocyte morphology and cell lysis; and i) Deionized water is the solvent for the formulation, and when added in small amounts or in excess, the final composition is no longer partially isotonic, which leads to morphological changes and cell death.

Exhaustive research and practical tests were carried out to determine the maximum and minimum amounts of each component used in the formulation for counting and morphological inference of erythrocytes and platelets. The tests that were performed to determine the minimum and maximum amount of each component of the composition for counting and morphological inference of erythrocytes and platelets (final composition) are shown below. All tests were performed following the same methodology.

Test methodology to determine the component ranges was as follows: a 1 μl sample of fresh capillary blood was diluted and homogenized in 199 μl of the final composition and, subsequently, 10 μl of this mixture was inserted into a hemocytometer for evaluation under an optical microscope. The evaluated parameters were: formulation stability, morphological characteristics of cells in contact with the final composition, cell lysis, and colonization by invading microorganisms. Tests 1 to 34 were performed to determine the minimum and maximum amount, as well as the preferred formulation.

Tests 1 to 4 determined the minimum and maximum amount of methylparaben are listed in table 1.

TABLE 1

Tests 1 to 4 for determination of amounts in % by mass of methylparaben.

| Compound | 1 | 2 | 3 | 4 |
|---|---|---|---|---|
| methylparaben | 0.0008 | 0.0009 | 0.0090 | 0.0091 |
| Propylparaben | 0.0012 | 0.0012 | 0.0012 | 0.0012 |
| sodium chloride | 5.0163 | 5.0163 | 5.0163 | 5.0163 |
| Sodium bicarbonate | 1.4415 | 1.4415 | 1.4415 | 1.4415 |
| BSA | 0.8649 | 0.8649 | 0.8649 | 0.8649 |
| sodium citrate | 1.4415 | 1.4415 | 1.4415 | 1.4415 |
| potassium citrate | 0.5189 | 0.5189 | 0.5189 | 0.5189 |
| $K_2EDTA$ | 1.7297 | 1.7297 | 1.7297 | 1.7297 |
| Deionized water | 88.9852 | 88.9851 | 88.9770 | 88.9769 |

Test 1: Determination of the minimum methylparaben value of 0.0008%. The amount added was not enough to avoid colonization of the composition by invading agents. Therefore, this composition was disapproved.

Test 2: Determination of the minimum value of 0.0009% methylparaben. The amount of methylparaben added was sufficient to prevent colonization of the composition by invading agents. Therefore, this composition was approved.

Test 3: Determination of the maximum value of methylparaben of 0.0090%. This maximum amount of methylparaben prevented the colonization of the composition by invading agents and did not cause cell death. Therefore, this composition was approved.

Test 4: Determination of the maximum value of methylparaben of 0.0091%. The amount that was added prevented the colonization of the composition by invading agents but caused cell death. Therefore, this composition was disapproved.

Tests 5 to 8 determined the minimum and maximum amount of propylparaben are listed in table 2.

TABLE 2

Tests 5 to 8 for determination of amounts in % by mass of propylparaben.

| Compound | 5 | 6 | 7 | 8 |
|---|---|---|---|---|
| methylparaben | 0.0045 | 0.0045 | 0.0045 | 0.0045 |
| Propylparaben | 0.0001 | 0.0002 | 0.0025 | 0.0026 |
| sodium chloride | 5.0163 | 5.0163 | 5.0163 | 5.0163 |
| Sodium bicarbonate | 1.4415 | 1.4415 | 1.4415 | 1.4415 |
| BSA | 0.8649 | 0.8649 | 0.8649 | 0.8649 |
| sodium citrate | 1.4415 | 1.4415 | 1.4415 | 1.4415 |
| potassium citrate | 0.5189 | 0.5189 | 0.5189 | 0.5189 |
| $K_2$EDTA | 1.7297 | 1.7297 | 1.7297 | 1.7297 |
| Deionized water | 88.9826 | 88.9825 | 88.9802 | 88.9801 |

Test 5: Determination of the minimum value of 0.0001% propylparaben. The amount added was not enough to avoid colonization of the composition by invading agents. Therefore, this composition was disapproved.

Test 6: Determination of the minimum value of 0.0002% propylparaben. The amount of propylparaben added was sufficient to prevent colonization of the composition by invading agents. Therefore, this composition was approved.

Test 7: Determination of the maximum value of 0.0025% propylparaben. This maximum amount of propylparaben prevented the colonization of the composition by invading agents and did not cause cell death. Therefore, this composition was approved.

Test 8: Determination of the maximum value of 0.0026% propylparaben. The amount that was added caused cell death. Therefore, this composition was disapproved.

Tests 9 to 12 determined the minimum and maximum amount of sodium chloride are listed in table 3.

TABLE 3

Tests 9 to 12 for determination of amounts in % by mass of sodium chloride.

| Compound | 9 | 10 | 11 | 12 |
|---|---|---|---|---|
| methylparaben | 0.0045 | 0.0045 | 0.0045 | 0.0045 |
| Propylparaben | 0.0012 | 0.0012 | 0.0012 | 0.0012 |
| sodium chloride | 0.2323 | 0.2324 | 11.4266 | 11.4267 |
| Sodium bicarbonate | 1.4415 | 1.4415 | 1.2300 | 1.2300 |
| BSA | 5.4000 | 5.4000 | 0.4000 | 0.4000 |
| sodium citrate | 1.4415 | 1.4415 | 0.7500 | 0.7500 |
| potassium citrate | 0.5189 | 0.5189 | 0.3000 | 0.3000 |
| $K_2$EDTA | 1.7297 | 1.7297 | 1.2000 | 1.2000 |
| Deionized water | 89.2304 | 89.2303 | 84.6877 | 84.6876 |

Test 9: Determination of the minimum amount of sodium chloride of 0.2323%. This amount of sodium chloride made the composition no longer partially isotonic and promoted cell lysis. Therefore, this composition was disapproved.

Test 10: Determination of the minimum amount of sodium chloride of 0.2324%. This added amount kept the final composition partially isotonic and cell lysis did not occur. Therefore, this composition was approved.

Test 11: Determination of the maximum amount of sodium chloride of 11.4266%. The added amount kept the final composition partially isotonic, as well as preserving the erythrocyte morphology. Therefore, this composition was approved.

Test 12: Determination of the maximum amount of sodium chloride of 11.4267%. The high concentration of sodium chloride, remained partially isotonic, but promoted changes in erythrocyte morphology and cell lysis. Therefore, this composition was disapproved.

Tests 13 to 16 determined the minimum and maximum amount of sodium bicarbonate are listed in table 4.

TABLE 4

Tests 13 to 16 for determination of amounts in % by mass of sodium bicarbonate.

| Compound | 13 | 14 | 15 | 16 |
|---|---|---|---|---|
| methylparaben | 0.0045 | 0.0045 | 0.0045 | 0.0045 |
| Propylparaben | 0.0012 | 0.0012 | 0.0012 | 0.0012 |
| sodium chloride | 5.0163 | 5.0163 | 5.0163 | 5.0163 |
| Sodium bicarbonate | 0.0432 | 0.0433 | 3.4020 | 3.4021 |
| BSA | 0.8649 | 0.8649 | 0.8649 | 0.8649 |
| sodium citrate | 1.4415 | 1.4415 | 1.4415 | 1.4415 |
| potassium citrate | 0.5189 | 0.5189 | 0.5189 | 0.5189 |
| $K_2$EDTA | 1.7297 | 1.7297 | 1.7297 | 1.7297 |
| Deionized water | 90.3798 | 90.3797 | 87.0210 | 87.0209 |

Test 13: Determination of the minimum amount of sodium bicarbonate of 0.0432%. This amount of sodium bicarbonate caused the composition to stop being partially isotonic and promoted cell lysis. Therefore, this composition was disapproved.

Test 14: Determination of the minimum amount of sodium bicarbonate of 0.0433%. This added amount kept the final composition partially isotonic and cell lysis did not occur. Therefore, this composition was approved.

Test 15: Determination of the maximum amount of sodium bicarbonate of 3.4020%. The amount added maintained the final composition partially isotonic, as well as preserving the erythrocyte morphology. Therefore, this composition was approved.

Test 16: Determination of the maximum amount of sodium bicarbonate of 3.4021%. The high concentration of sodium bicarbonate promoted changes in erythrocyte morphology and cell lysis. Therefore, this composition was disapproved.

Tests 17 to 19 determined the minimum and maximum amount of bovine serum albumin are listed in table 5.

TABLE 5

Tests 17 to 19 to determine the amounts in % mass of bovine serum albumin

| Compound | 17 | 18 | 19 |
|---|---|---|---|
| methylparaben | 0.0045 | 0.0045 | 0.0045 |
| Propylparaben | 0.0012 | 0.0012 | 0.0012 |
| sodium chloride | 5.0163 | 1.0000 | 1.0000 |
| Sodium bicarbonate | 1.4415 | 1.2300 | 1.2300 |
| BSA | 0.0000 | 10.6198 | 10.6199 |
| sodium citrate | 1.4415 | 0.7500 | 0.7500 |
| potassium citrate | 0.5189 | 0.3000 | 0.3000 |
| $K_2$EDTA | 1.7297 | 1.2000 | 1.2000 |
| Deionized water | 89.8464 | 84.8945 | 84.8944 |

Test 17: Determination of the minimum amount of 0% bovine serum albumin. The final composition works satisfactorily in the absence of BSA. Therefore, this composition was approved.

Test 18: Determination of the maximum amount of bovine serum albumin of 10.6198%. The added amount caused the final composition to maintain the morphological characteristics of the erythrocytes and increased the stability of the final composition. Therefore, this composition was approved.

Test 19: Determination of the maximum amount of bovine serum albumin of 10.6199%. The increase in bovine serum albumin concentration promoted changes in erythrocyte morphology and cell lysis. Therefore, this composition was disapproved.

Tests 20 to 22 determined the minimum and maximum amount of sodium citrate are listed in table 6.

TABLE 6

Tests 20 to 22 to determine the amounts in % by mass of sodium citrate

| Compound | 20 | 21 | 22 |
|---|---|---|---|
| methylparaben | 0.0045 | 0.0045 | 0.0045 |
| Propylparaben | 0.0012 | 0.0012 | 0.0012 |
| sodium chloride | 5.0163 | 5.0163 | 5.0163 |
| Sodium bicarbonate | 1.4415 | 1.4415 | 1.4415 |
| BSA | 0.8649 | 0.8649 | 0.8649 |
| sodium citrate | 0.0000 | 4.1690 | 4.1691 |
| potassium citrate | 0.5189 | 0.5189 | 0.5189 |
| $K_2$EDTA | 1.7297 | 1.7297 | 1.7297 |
| Deionized water | 90.4230 | 86.2540 | 86.2539 |

Test 20: Determination of the minimum amount of 0% sodium citrate. The final composition works satisfactorily in the absence of sodium citrate. Therefore, this composition was approved.

Test 21: Determination of the maximum amount of sodium citrate of 4.1690%. The added amount caused the final composition to maintain the morphological characteristics of the erythrocytes. Therefore, this composition was approved.

Test 22: Determination of the maximum amount of sodium citrate of 4.1691%. The high concentration of sodium citrate promoted changes in erythrocyte morphology and cell lysis. Therefore, this composition was disapproved.

Tests 23 to 25 determined the minimum and maximum amount of potassium citrate are listed in table 7.

TABLE 7

Tests 23 to 25 to determine the amounts in % by mass of potassium citrate

| Compound | 23 | 24 | 25 |
|---|---|---|---|
| methylparaben | 0.0045 | 0.0045 | 0.0045 |
| Propylparaben | 0.0012 | 0.0012 | 0.0012 |
| sodium chloride | 5.0163 | 5.0163 | 5.0163 |
| Sodium bicarbonate | 1.4415 | 1.4415 | 1.4415 |
| BSA | 0.8649 | 0.8649 | 0.8649 |
| sodium citrate | 1.4415 | 1.4415 | 1.4415 |
| potassium citrate | 0.0000 | 0.5296 | 0.5297 |
| $K_2$EDTA | 1.7297 | 1.7297 | 1.7297 |
| Deionized water | 89.5004 | 88.9708 | 88.9707 |

Test 23: Determination of the minimum amount of 0% potassium citrate. The final composition works satisfactorily in the absence of potassium citrate. Therefore, this composition was approved.

Test 24: Determination of the maximum amount of potassium citrate of 0.5296%. The added amount caused the final composition to maintain the morphological characteristics of the erythrocytes. Therefore, this composition was approved.

Test 25: Determination of the maximum amount of potassium citrate of 0.5297%. The high concentration of potassium citrate promoted changes in erythrocyte morphology and cell lysis. Therefore, this composition was disapproved.

Tests 26 to 29 determined the minimum and maximum amount of $K_2$EDTA are listed in table 8.

TABLE 8

Tests 26 to 29 to determine the amounts in % by mass of K 2 EDTA

| Compound | 26 | 27 | 28 | 29 |
|---|---|---|---|---|
| methylparaben | 0.0045 | 0.0045 | 0.0045 | 0.0045 |
| Propylparaben | 0.0012 | 0.0012 | 0.0012 | 0.0012 |
| sodium chloride | 5.0163 | 5.0163 | 1.1000 | 1.1000 |
| Sodium bicarbonate | 1.4415 | 1.4415 | 0.5000 | 0.5000 |
| BSA | 0.8649 | 0.8649 | 0.8649 | 0.8649 |
| sodium citrate | 1.4415 | 1.4415 | 0.5200 | 0.5200 |
| potassium citrate | 0.5189 | 0.5189 | 0.5189 | 0.5189 |
| $K_2$EDTA | 0.0870 | 0.0871 | 10.7809 | 10.7810 |
| Deionized water | 90.6242 | 90.6241 | 85.7096 | 85.7095 |

Test 26: Determination of the minimum amount of $K_2$EDTA of 0.0870%. This amount of $K_2$EDTA promoted platelet aggregation and platelet count errors. Therefore, this composition was disapproved.

Test 27: Determination of the minimum amount of $K_2$EDTA of 0.0871%. This added amount kept the platelets without aggregating and maintained the cell morphology. Therefore, this composition was approved.

Test 28: Determination of the maximum amount of $K_2$EDTA of 10.7809%. This added amount kept the cell morphology preserved and the platelets without aggregation, and cell lysis did not occur. Therefore, this composition was approved.

Test 29: Determination of the maximum amount of $K_2$EDTA of 10.7810%. The high concentration of $K_2$EDTA promoted changes in erythrocyte morphology and cell lysis. Therefore, this composition was disapproved.

Tests 30 to 33 determined the minimum and maximum amount of deionized water are listed in table 9.

TABLE 9

Tests 30 to 33 to determine the amounts in % by mass of deionized water

| Compound | 30 | 31 | 32 | 33 |
|---|---|---|---|---|
| methylparaben | 0.0045 | 0.0045 | 0.0045 | 0.0045 |
| Propylparaben | 0.0012 | 0.0012 | 0.0012 | 0.0012 |
| sodium chloride | 5.0163 | 5.0163 | 0.5450 | 0.5449 |
| Sodium bicarbonate | 1.4415 | 1.4415 | 1.4415 | 1.4415 |
| BSA | 0.8649 | 0.8649 | 0.9000 | 0.9000 |
| sodium citrate | 3.2000 | 3.2000 | 1.4415 | 1.4415 |
| potassium citrate | 0.5189 | 0.5189 | 0.5189 | 0.5189 |
| $K_2$EDTA | 4.4827 | 4.4826 | 1.7300 | 1.7300 |
| Deionized water | 84.4700 | 84.4701 | 93.4174 | 93.4175 |

Test 30: Determination of the minimum amount of deionized water of 84.4700%. The final composition was no longer partially isotonic with this amount of deionized water, there were morphological changes and cell death. Therefore, this composition was disapproved.

Test 31: Determination of the minimum amount of deionized water of 84.4701%. This added amount kept the composition partially isotonic, there were no significant morphological changes, nor cell death. Therefore, this composition was approved.

Test 32: Determination of the maximum amount of deionized water of 93.4174%. This added amount kept the composition partially isotonic, there were no significant morphological changes, nor cell death. Therefore, this composition was approved.

Test 33: Determination of the maximum amount of deionized water of 93.4175%. The final composition was no longer partially isotonic with this amount of deionized water, there were morphological changes and cell death. Therefore, this composition was disapproved.

In summary, the maximum and minimum amounts of the mass percentages of the components for the satisfactory functioning of the formulation for counting and morphological inference of erythrocytes and platelets are listed in table 10 below:

TABLE 10

Minimum and maximum amounts of components of the final composition in % by mass.

| Compound | Min (%) | Max (%) |
|---|---|---|
| methylparaben | 0.0009 | 0.0090 |
| Propylparaben | 0.0002 | 0.0025 |
| sodium chloride | 0.2324 | 11.4266 |
| Sodium bicarbonate | 0.0433 | 3.4020 |
| BSA | 0.0000 | 10.6198 |
| sodium citrate | 0.0000 | 4.1690 |
| potassium citrate | 0.0000 | 0.5296 |
| $K_2EDTA$ | 0.0871 | 10.7809 |
| Deionized water | 84.4701 | 93.4174 |

Test 34 determined the preferential amount of the components of the composition is listed in table 11. In this test, the final composition showed the best results in terms of cell morphology and stability, avoided contamination by invading microorganisms and the formation of cell aggregates, preserving the erythrocytes.

TABLE 11

Test 34 with preferred composition, amount in % by mass.

| Compound | % by mass |
|---|---|
| methylparaben | 0.0045 |
| Propylparaben | 0.0012 |
| sodium chloride | 5.0163 |
| Sodium bicarbonate | 1.4415 |
| BSA | 0.8649 |
| sodium citrate | 1.4415 |
| potassium citrate | 0.5189 |
| $K_2EDTA$ | 1.7297 |
| Deionized water | 88.9815 |

The formulation for counting and morphological inference of erythrocytes and platelets can be used in venous blood with EDTA or in fresh capillary in the proportion of 1:100 to 1:200 parts by volume. After diluting the collected blood, the blood mixture and final composition must be homogenized and inserted into a hemocytometer for reading under an optical microscope, or in a Point-of-Care device, for analysis with a 10× or 40× magnifying objective lens. The formulation for counting and morphological inference of erythrocytes and platelets was evaluated with blood from rats, dogs, cats and horses, showing good results, and can also be used for veterinary purposes. The final composition can be stored for long periods of up to 4 months, provided it is protected from light.

The invention claimed is:

1. A formulation for counting and morphological-based inferencing of erythrocytes and platelets that preserves the morphology of erythrocytes and platelets, comprising deionized water in a range of 84.4701% to 93.4174% by mass, and the following compounds in the indicated mass percentages:

| Compound | Min (%) | Max (%) |
|---|---|---|
| methyl paraben | 0.0009 | 0.0090 |
| Propylparaben | 0.0002 | 0.0025 |
| sodium chloride | 0.2324 | 11.4266 |
| Sodium bicarbonate | 0.0433 | 3.4020 |
| Bovine serum albumin (BSA) | 0.0000 | 10.6198 |
| sodium citrate | 0.0000 | 4.1690 |
| potassium citrate | 0.0000 | 0.5296 |
| $K_2EDTA$ | 0.0871 | 10.7809. |

2. The formulation for counting and morphological-based inferencing of erythrocytes and platelets according to claim 1, comprising 88.9815% by mass of deionized water, 1.7297% by mass of $K_2EDTA$ and comprising the following compounds, in the following mass percentages:

| Compound | % by mass |
|---|---|
| methylparaben | 0.0045 |
| Propylparaben | 0.0012 |
| sodium chloride | 5.0163 |
| Sodium bicarbonate | 1.4415 |
| (bovine serum albumin (BSA) | 0.8649 |
| sodium citrate | 1.4415 |
| potassium citrate | 0.5189. |

3. A method for preparation of a formulation for counting and morphological-based inferencing of erythrocytes and platelets according to claim 1, comprising the following steps:

1) either i) preparing a preservative formulation, by weighing methylparaben and propylparaben each in an amount within the ranges recited in claim 1, followed by dilution in deionized water; homogenizing the preservative formulation on a thermal magnetic plate heated to 100° C., until complete dilution of the aforementioned compounds; or ii) providing a preservative formulation comprising 5-chloro-2-methyl-4-isothiazolin-3-one and 2-methyl-4-isothiazolin-3-one (3% by mass) dispersed in modified glycol (93-95% by mass) and alkyl carboxylate (2-3% by mass);

2) preparing an isotonic formulation, by weighing sodium bicarbonate, sodium chloride, bovine serum albumin (BSA), sodium citrate, potassium citrate and $K_2EDTA$ wherein each component is present in an amount within the ranges recited in claim 1, followed by dilution in deionized water; and

3) preparing a final composition by mixing the preservative formulation with the isotonic formulation, followed by filtration through No. 1 filter paper, and buffering to obtain a pH measurement in a range between 7.5 and 9.5.

4. A method of counting erythrocytes and platelets in an animal blood sample comprising the steps of diluting and homogenizing the blood sample in the formulation according to claim 1 to obtain a mixture and inserting the mixture into a hemocytometer for evaluation under an optical microscope.

* * * * *